United States Patent
Horiuchi et al.

(10) Patent No.: US 7,064,209 B2
(45) Date of Patent: Jun. 20, 2006

(54) PROCESS FOR PRODUCING OPTICALLY ACTIVE OXOHEPTENOIC ACID ESTER

(75) Inventors: Takashi Horiuchi, Funabashi (JP); Masamichi Shimizu, Funabashi (JP); Shoichi Kondo, Funabashi (JP); Tadashi Soejima, Hiratsuka (JP); Kazuhiro Umeo, Hiratsuka (JP)

(73) Assignees: Nissan Chemical Industries, Ltd., Tokyo (JP); Sankyo Chemical Industries, Ltd., Tokyo (JP)

(*) Notice: Subject to any disclaimer, the term of this patent is extended or adjusted under 35 U.S.C. 154(b) by 60 days.

(21) Appl. No.: 10/495,268

(22) PCT Filed: Nov. 14, 2002

(86) PCT No.: PCT/JP02/11870

§ 371 (c)(1),
(2), (4) Date: Jun. 4, 2004

(87) PCT Pub. No.: WO03/042180

PCT Pub. Date: May 22, 2003

(65) Prior Publication Data

US 2005/0054853 A1    Mar. 10, 2005

(30) Foreign Application Priority Data

Nov. 14, 2001  (JP) .............................. 2001-348569

(51) Int. Cl.
*C07D 215/14*    (2006.01)
(52) U.S. Cl. ...................................... 546/173
(58) Field of Classification Search ................. 546/173
See application file for complete search history.

(56) References Cited

U.S. PATENT DOCUMENTS 6,835,838 B1 * 12/2004 Chen et al. ................. 546/173

FOREIGN PATENT DOCUMENTS

JP         A 08-092217        4/1996

OTHER PUBLICATIONS

"Tetrahedron Asymmetry" Soriente et al.; vol. 11; pp. 2255-2258; 2000.
"Tetrahedron Asymmetry" Soriente et al.; vol. 12; pp. 959-963; 2001.
"Synthesis" Wang et al.; pp. 291-292; Apr. 1989.
"Chemistry Letters" Tsuji et al.; pp. 649-652; 1978.

* cited by examiner

Primary Examiner—D. Margaret Seaman
(74) Attorney, Agent, or Firm—Oliff & Berridge, PLC

(57) ABSTRACT

A novel process for producing an optically active (E)-7-[2-cyclopropyl-4-(4-fluorophenyl quinolin-3-yl]-5-hydroxy-3-oxohept-6-enoic acid ester of formula (III) which is important as an intermediate for synthesizing medicines, comprises reacting 1,3-bis(trimethylsilyloxy)-1-alkoxybuta-1,3-diene of formula (I) with (E)-3-[2-cyclopropyl-4-(4-fluorophenyl)-quinolin-3-yl]-prop-2-en-1-al of formula (II) in the presence of an optically active binaphthol-titanium complex obtained from 1,1'-bi-2-naphthol with titanium tetraisopropoxide, a metal salt and an amine, and then subjecting the reaction product to desilylation

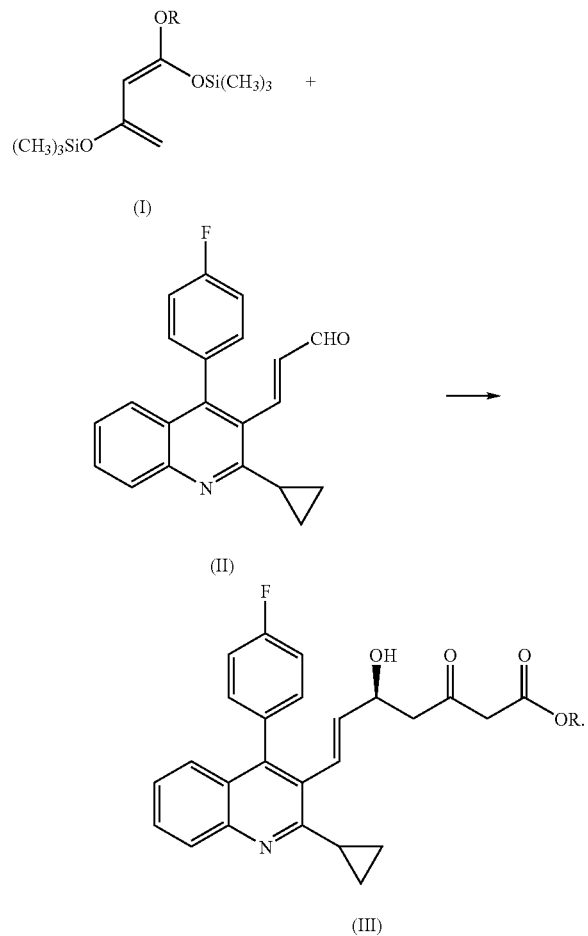

4 Claims, No Drawings

PROCESS FOR PRODUCING OPTICALLY ACTIVE OXOHEPTENOIC ACID ESTER

This is a National Stage of PCT/JP02/11870, filed Nov. 14, 2002, and claims priority from Japanese Patent Application No. 2001-348569, filed Nov. 14, 2001.

TECHNICAL FIELD

The present invention relates to a process for producing an optically active (E)-7-[2-cyclopropyl-4-(4-fluorophenyl) quinolin-3-yl]-5-hydroxy-3-oxohept-6-enoic acid ester which is an intermediate for synthesizing (3R,6S,6E)-7-[2-cyclopropyl-4-(4-fluorophenyl)quinolin-3-yl]-3,5-dihydroxyhept-6-enoic acid salt useful for prevention and treatment of hyperlipidemia, arteriosclerosis or the like.

BACKGROUND ART

It is known that an optically active (E)-7-[2-cyclopropyl-4-(4-fluorophenyl) quinolin-3-yl]-5-hydroxy-3-oxohept-6-enoic acid ester (hereinafter referred to as compound (III)) of formula (III)

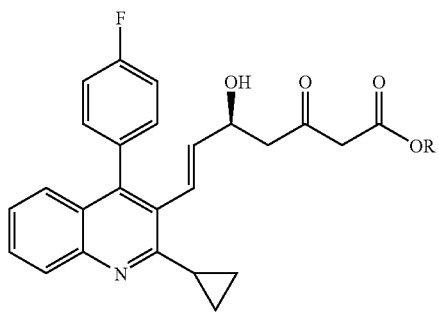

(III)

wherein R is an alkyl having 1 to 4 carbon atoms which is a desired compound of the present invention, is produced by reacting (E)-3-[2-cyclopropyl-4-(4-fluorophenyl)-quinolin-3-yl]-prop-2-en-1-al (hereinafter referred to as compound (II)) of formula (II)

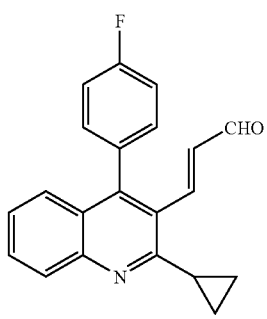

(II)

with diketene in an organic solvent in the presence of an optically active Schiff base-titanium complex prepared by reacting an optically active Schiff base with a titanium compound (Japanese Patent Laid-open No. Hei 8-92217).

In addition, Tetrahedron Asymmetry, Vol. 11, 2255–2258 (2000) and Tetrahedron Asymmetry, Vol. 12, 959–963 (2001) describe processes for producing an optically active alcohol by reacting 1,3-bis(trimethylsilyloxy)-1-alkoxybuta-1,3-diene (hereinafter referred to as compound (I)) of formula (I)

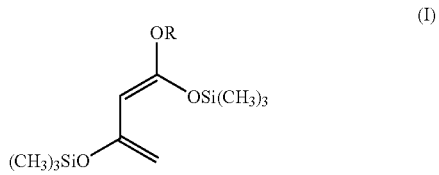

(I)

wherein R is an alkyl having 1 to 4 carbon atoms, with an aldehyde in the presence of an optically active binaphthol-titanium complex.

However, the process disclosed in Japanese Patent Laid-open No. Hei 8-92217 is troublesome as it requires a plurality of steps for preparing the optically active Schiff base-titanium complex. Further, the optical purity of compound (III) produced by the process is about 78% ee, therefore a further optical resolution is required for obtaining compound (III) having such a high optical purity that it can be used as an intermediate for synthesis.

In addition, the process disclosed in Tetrahedron Asymmetry, Vol. 11, 2255–2258 (2000) and Tetrahedron Asymmetry, Vol. 12, 959–963 (2001) give desired compounds in a relatively high yield and optical purity, but it requires not only strict reaction conditions, such as distillation and purification of a solvent to be used but also an addition of a molecular sieve dried at a high temperature during the preparation of the complex. Thus, it is hard to regard the process as a practical one.

DISCLOSURE OF INVENTION

To dissolve the above mentioned problems, the present inventors have made extensive research and have found out that the optical purity and reaction yield are greatly improved by adding a metal salt and various amines in a reaction system between compound (I) and compound (II) in the presence of an optically active binaphthol-titanium complex which can be easily prepared by reacting 1,1'-bi-2-naphthol with titanium tetraisopropoxide. Further, it was found out that desired compounds (III) are produced in an optical purity of 99% ee or more and a yield of 85% or more by subjecting the reaction mixture to desilylation in the reaction system as it is.

That is, the present invention relates to a process for producing an optically active (E)-7-[2-cyclopropyl-4-(4-fluorophenyl)quinolin-3-yl]-5-hydroxy-3-oxohept-6-enoic acid ester of formula (III)

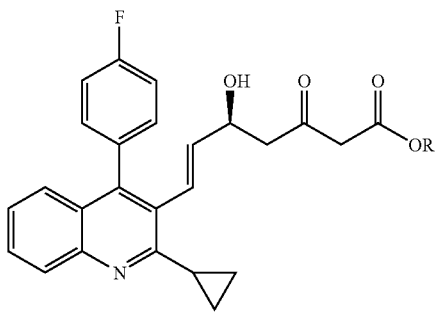

(III)

wherein R is an alkyl having 1 to 4 carbon atoms, which comprises reacting 1,3-bis(trimethylsilyloxy)-1-alkoxybuta-1,3-diene of formula (I)

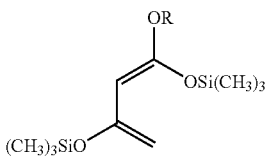

(I)

wherein R is as defined above, with (E)-3-[2-cyclopropyl-4-(4-fluorophenyl)-quinolin-3-yl]-prop-2-en-1-al of formula (II)

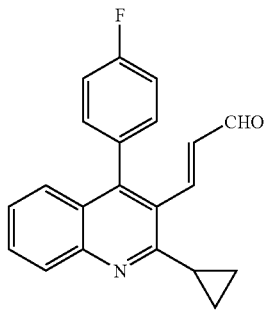

(II)

in the presence of an optically active binaphthol-titanium complex prepared by reacting 1,1'-bi-2-naphthol with titanium tetraisopropoxide, a metal salt and an amine, and then subjecting the resulting reaction product to desilylation.

BEST MODE FOR CARRYING OUT THE INVENTION

The optically active binaphthol-titanium complex used in the production process according to the present invention can be easily prepared by for example reacting (S)-(−)- or (R)-(+)-1,1'-bi-2-naphthol with titanium tetraisopropoxide in an organic solvent such as toluene, benzene, methylene chloride or diethyl ether according to the method of Ji-Tao Wang et al. (Synthesis, 291–292 (1989)). The compounds prepared as above can be used in the next step without isolation.

The titanium tetraisopropxide used for preparing the optically active binaphthol-titanium complex is used in an amount of 0.5 to 2.3 mol, preferably 0.85 to 1.15 mol based on 1 mol of optically active 1,1'-bi-2-naphthol.

The optically active binaphthol-titanium complex for producing compound (III) is used in an amount of 0.001 to 1 mol, preferably 0.02 to 0.06 mol based on 1 mol of compound (II).

In compound (I) used in the production process according to the present invention, R in formula (I) is an alkyl having 1 to 4 carbon atoms, and preferably compounds of formula (I) wherein R is methyl or ethyl can be used.

Compound (I) can be produced based on the process of Tsuji et al. (Chem. Letter., 649 (1978)) according to a process comprising reacting an acetoacetic acid alkyl ester with trimethylsilyl chloride to produce 3-(trimethylsilyloxy)but-2-enoic acid alkyl ester, and reacting the ester at first with lithium isopropylamide and then with trimethylsilyl chloride.

Compound (I) in the production of compound (III) is used in an amount of 1 to 5 mol, preferably 1 to 3 mol based on 1 mol of compound (II).

The metal salt added in the production of compound (III) includes lithium salts such as lithium chloride, lithium bromide, lithium acetate, lithium hydroxide, lithium borate or lithium phosphate, and salts of metal other than lithium, such as sodium chloride, potassium chloride, magnesium chloride, aluminum chloride or copper chloride. Although the metal salt is selected depending on the amount and kind of amines used, the concentration of optically active binaphthol-titanium complex or the concentration of compound (II), lithium salts among these salts afford preferable results, and lithium chloride is more preferable among the lithium salts.

The amount used of the metal salt depends on the amount of optically active binaphthol-titanium complex and amine which are added together, or the concentration of reaction solution, but in a case where lithium chloride is used, it is used in an amount of 0.03 to 1.0 mol, preferably 0.1 to 0.4 mol based on 1 mol of compound (II).

The amine added in the production of compound (III) includes N,N,N',N'-tetramethylethylenediamine, diisopropylethylamine, pyridine, 4-dimethylaminopyridine, triethylamine, morpholine and the like. N,N,N',N'-tetramethylethylenediamine, diisopropylethylamine, pyridine and 4-dimethylaminopyridine afford preferable results, and among them N,N,N',N'-tetramethylethylenediamine is more preferable.

The amount used of the amine depends on the kind of amine used, the amount of optically active binaphthol-titanium complex and the metal salt which are added together, or the concentration of reaction solution, but in a case where N,N,N',N'-tetramethylethylenediamine is used, it is used in an amount of 0.03 to 2.0 mol, preferably 0.1 to 1.2 mol from a viewpoint of effect on the post-treatment of the reaction based on 1 mol of compound (II).

If the amine does not take part in the reaction, it can be added in the step for producing compound (I).

When lithium chloride and N,N,N',N'-tetramethylethylenediamine are used for producing compound (III) according to the present invention, the amount used of them depends on the amount of optically active binaphthol-titanium complex added together or the concentration of the reaction solution, but is 0.03 to 1.0 mol of lithium chloride and 0.03 to 2.0 mol of N,N,N',N'-tetramethylethylenediamine, preferably 0.1 to 0.4 mol of lithium chloride and 0.1 to 1.2 mol of N,N,N',N'-tetramethylethylenediamine based on 1 mol of compound (II).

The process of the present invention can be carried out by reacting compound (I) with compound (II) under a flow of an inert gas such as nitrogen gas, helium gas or argon gas, in the presence of an optically active binaphthol-titanium complex, a metal salt and an amine, in organic solvents.

The organic solvent used is not specifically limited unless it takes part in the reaction, and generally ether solvents such as tetrahydrofuran, diethyl ether or diisopropyl ether can be used, and tetrahydrofuran is preferable. The amount used of the organic solvent is not specifically limited, and is generally 1 to 100 times (mass ratio), preferably 5 to 30 times (mass ratio) based on compound (II).

The reaction temperature depends on the kind and amount of the organic solvent used, and is generally −20 to 55° C., preferably 0 to 45° C.

The reaction time depends on the concentration of compound (II) used, the kind and amount of optically active binaphthol-titanium complex and solvent used, the reaction temperature and the like, and is generally 2 to 12 hours, preferably 2 to 6 hours.

Upon completion of the reaction, the reaction is ceased by adding water or various aqueous solutions to the reaction mixture and stirring. In general, water, aqueous solution of sodium bicarbonate, saline solution, aqueous solution of sodium carbonate, aqueous ammonia, aqueous solution of tartrate or the like can be used, and aqueous solution of sodium bicarbonate or saline solution is preferable. The concentration thereof is not specifically limited, but aqueous solution of sodium bicarbonate is preferably used in a concentration of 3.5% to saturation, and saline solution is preferably used in a concentration of 10% to saturation. The amount used of the aqueous solution depends on the concentration and kind thereof, but in a case where a saturated aqueous solution of sodium bicarbonate is used, it is generally used in amount of 0.1 to 10 times (volume ratio), preferably 0.1 to 5 times (volume ratio) based on the reaction mixture.

The method for extracting the reaction product from the reaction mixture depends on the kind of the reaction solvent. In a case where tetrahydrofuran is used as solvent for reaction, the reaction product is extracted with an organic solvent after evaporating tetrahydrofuran under a reduced pressure. The organic solvent is not specifically limited unless it is freely miscible with water, and ethyl acetate, diethyl ether, toluene and the like can be used, and ethyl acetate is preferable. The amount used of the organic solvent is not specifically limited, and is generally 0.1 to 10 times (volume ratio), preferably 0.5 to 2 times (volume ratio) based on the reaction mixture.

For the removal of silyl group from the reaction product and the purification of compound (III) produced by the removal of the silyl group, a salt of compound (III) with an acid is precipitated by adding the acid to the above-mentioned extraction solution and stirring, and the precipitated salt is filtered off. The acid used may be an inorganic acid such as sulfuric acid or hydrochloric acid, and is preferably sulfuric acid. The salt filtered off is neutralized with an aqueous alkaline solution, extracted with an organic solvent and crystallized to obtain a desired compound. The aqueous alkaline solution used for the cleavage of salt includes aqueous solution of alkaline metal carbonate, such as aqueous solution of sodium bicarbonate or aqueous solution of sodium carbonate, aqueous solution of alkaline metal such as aqueous solution of sodium hydroxide, aqueous ammonia and the like, and is preferably aqueous solution of sodium carbonate.

As compound (III) produced as mentioned above has a high optical purity of 99% ee, it has a quality for making it fully possible to use as such as an intermediate for synthesizing (3R,5S,6E)-7-[2-cyclopropyl-4-(4-fluorophenyl) quinolin-3-yl]-3,5-dihydroxyhept-6-enoic acid salt useful for prevention and treatment of hyperlipidemia, arteriosclerosis or the like.

EXAMPLES

Hereinafter, the present invention will be illustrated based on examples to which the present invention is not limited.

In the meanwhile, the optical purity (% ee) of each optical isomer was measured with high performance liquid chromatography (HPLC) under the following conditions:
Column: CHIRALPAK AD (manufactured by Daicel Chemical Industries, Ltd.)
Mobile phase: hexane:ethanol=95:5
Flow rate: 1.0 mL/min.
Detection wavelength: 254 nm In addition, the progress level of the reaction in examples was measured with high performance liquid chromatography (HPLC) under the following conditions:
Column: L-Column-ODS (manufactured by Japan Chemicals Evaluation and Research Institute)
Mobile phase: gradient condition (analysis is started from 0.01 M ammonium acetate buffer (pH 5.3): acetonitrile=60:40, and 40 minutes later the ratio is 10:90)
Flow rate: 1.0 mL/min.
Detection wavelength: 254 nm Reference Example 1

Production of
1,3-bis(trimethylsilyloxy)-1-ethoxybuta-1,3-diene

1) Production of 3-(trimethylsilyloxy) but-2-enoic acid ethyl ester 182.21 g (1.4 mol) of ethyl acetoacetate and 169.98 g (1.4 mol) of triethylamine were dissolved in a mixed solvent of 182 mL of tetrahydrofuran and 1.64 L of hexane under nitrogen atmosphere. To this solution, 167.3 g (1.54 mol) of trimethylsilyl chloride was added dropwise at a temperature of 21 to 45° C., and then the solution was stirred at 25° C. for 3 hours. The reaction mixture was cooled to 10° C., the reaction was ceased by adding 547 mL of water thereto and an organic layer was separated. The organic layer was washed two times with 273 mL of water, dried over 54.7 g of anhydrous magnesium sulfate, and then filtered. The solvent was evaporated to obtain 301.3 g (crude yield 106.4%) of 3-(trimethylsilyloxy) but-2-enoic acid ethyl ester.

2) Production of 1,3-bis(trimethylsilyloxy)-1-ethoxybuta-1,3-diene

Under nitrogen atmosphere, 28.13 g (0.28 mol) of diisopropylamine was dissolved in 240 mL of tetrahydrofuran, and the resulting solution was cooled to −20° C. To the solution, 100.3 mL (0.27 mol) of n-butyl lithium/n-hexane solution with a concentration of 2.66 mol/L was added dropwise, and stirred at −30 to −20° C. for 30 minutes. The reaction mixture was cooled to −80° C., and 45.0 g (0.22 mol) of 3 (trimethylsilyloxy) but-2-enoic add ethyl ester was added dropwise to the solution at −80 to −93° C., stirred at −90° C. for 1 hour, and then 31.4 g (0.29 mol) of trimethylsilyl chloride was added dropwise thereto at −100° C. and stirred for 3 hours. The solvent was evaporated at a room temperature under a reduced pressure, te residue was dissolved in 585 mL of n-hexane. The solution was stirred at a temperature of 0 to 5° C. for 1 hour, allowed to stand for 14 hours and the precipitated insoluble material was filtered off. The filtrate was concentrated under a reduced pressure to obtain 59.85 g of 1,3-bis(trimethylsilyloxy)-1-ethoxybuta-1,3-diene as concentrated residue.

Example 1

Production of (5S,6E)-7-[2-cyclopropyl-4-(4-fluorophenyl)-quinolin-3-yl]-5-hydroxy-3-oxohept-6-enoic acid ethyl ester Under nitrogen atmosphere, 25.0 (0.079 mol) of (E)3-[2-cyclopropyl-4-(4-fluorophenyl)-quinolin-3-yl]-prop-2-en-1-al was dissolved in 305.0 g of tetrahydrofuran. To the solution, 6.35 g (0.0016 mol) of a mixed solution prepared by dissolving (S)-(−)-1,1'-bi-2-naphthol and titanium tetraisopropoxide to toluene was added at first, and then 1.10 g (0.026 mol) of lithium chloride and 6.14 g (0.053 mol) of N,N,N',N'-tetramethylethylenediamine were added, and 51.34 g of 1,3-bis(trimethylsilyloxy)-1-ethoxybuta-1,3-diene as concentrated residue obtained according to Reference Example 1 was added dropwise to the solution, and then stirred at a temperature of 27 to 30° C. for 4 hours.

The reaction was ceased by adding an aqueous solution comprising 32.5 mL of ion exchange water and 32.5 mL of saturated aqueous solution of sodium bicarbonate, tetrahydrofuran was evaporated under a reduced pressure, and an organic layer was extracted with 675 mL of ethyl acetate. The extracted solution was washed with 125 mL of ion exchange water and 125 mL of saturated aqueous solution of sodium bicarbonate, dried over 20 g of anhydrous magnesium sulfate and filtered.

The filtrate was cooled to 0° C. 23.9 g (0.118 mol) of 50% by weight sulfuric acid aqueous solution was added dropwise and stirred at a temperature of 0 to 5° C. for 2 hours. The resulting sulfate was filtered off, and washed two times with 25 mL of ethyl acetate.

The obtained sulfate in wet state was dispersed into a two-layer solvent comprising 250 mL of ethyl acetate and 100 mL of ion exchange water, 150 mL of 10% by weight sodium carbonate aqueous solution was added, and stirred at a temperature of 26 to 28° C. for 30 minutes. An organic layer was separated off, and 200 mL of ethyl acetate was added to an aqueous layer and then re-extracted. The extract together with the organic layer was washed with 125 mL of saturated saline solution, dried over 20 g of anhydrous sodium sulfonate and then filtered.

The filtrate was concentrated under a reduced pressure to about 70 g in a total mass, then 125 g of ethylcyclohexane was added and 60 g of the solvent was evaporated. The solution was cooled to 0 to 5° C. and further 250 g of ethylcyclohexane was added, and stirred for 2 hours. The precipitated crystal was filtered off, and dried under a reduced pressure to obtain 30.06 g of (5S,6E)-7-[2-cyclopropyl-4-(4-fluorophenyl)-quinolin-3-yl]-5-hydroxy-3 oxohept-6-enoic acid ethyl ester.

Optical purity: 99% ee
Yield based on (E)-3-[2-cyclopropyl-4-(4-fluorophenyl)-quinolin-3-yl]-prop-2-en-1-al: 85.2%
Melting point 90.6–92.0° C.
$^1$H-NMR (CDCl$_3$, 400 MHz, ppm) δ: 1.0–1.1 (m, 2H), 1.28 (t, J=7.3 Hz, 3H), 1.3–1.4 (m, 2H), 2.3–2.4 (s, 1H), 2.53 (s, 1H), 2.53 (d, J=3.0 Hz, 1H), 2.6–2.8 (m, 1H), 6.67 (s, 2H), 4.21 (q, J=7.3 Hz, 2H), 4.5–4.7 (m, 1H), 5.58 (dd, J=5.9 Hz, 16.1 Hz, 1H), 6.67 (dd, J=1.5 Hz, 16.1 Hz, 1H), 7.1–7.3 (m, 4H), 7.2–7.4 (m, 2H), 7.5–7.7 (m, 1H), 7.95 (d, J=8.3 Hz, 1H).

The following experiments were carried out in order to investigate an effect of the addition of lithium chloride and N,N,N',N'-tetramethylethylenediamine on reaction rate and optical purity.

Example 2

Experiment in which both Lithium Chloride and N,N,N',N'-tetramethylethylenediamine were Added Under nitrogen atmosphere, 1.0 g (3.15 mol) of (E)-[2-cyclopropyl-4-(4-fluorophenyl)-quinolin-3-yl]prop-2-en-1-al was dissolved in 12 mL of tetrahydrofuran. To the solution, 42.57 mg (0.0945 mmol) of optically active binaphthol-titanium complex powder prepared by reacting (S)-(−)-1,1'-bi-2-naphthol with titanium tetraisopropoxide in dichloromethane and then evaporating the solvent was added at first, and then 40.1 mg (0.945 mmol) of lithium chloride and 292.9 mg (2.52 mmol) of N,N,N',N'-tetramethylethylenediamine were added, and 1.73 g (6.3 mmol) of 1.3-bis(trimethylsilyloxy)-1-alkoxybuta-1,3-diene as concentrated residue obtained according to Reference Example 1 was added dropwise to the solution, and stirred at a temperature of 27 to 30° C.

The end point of the reaction was confirmed on 5 hours after the reaction was started in HPLC analysis with L-Column-ODS, and the optical purity based on CHIRALPAK AD was 99.9% ee or more.

Comparative Example 1

Experiment in which Neither Lithium Chloride Nor N,N,N',N'-tetramethylethylenediamine was Added Under nitrogen atmosphere, 1.0 g (3.15 mol) of (E)-3-[2-cyclopropyl-4-(4-fluorophenyl)-quinolin-3-yl]-prop-2-en-1-al was dissolved in 12 mL of tetrahydrofuran. To the solution, 42.57 mg (0.0945 mmol) of optically active binaphthol-titanium complex powder prepared by reacting (S)-(−)-1,1'-bi-2-naphthol with titanium tetraisopropoxide in dichloromethane and then evaporating the solvent was added at first, and then 1.73 g (6.3 mmol) of 1,3-bis(trimethylsilyloxy)-1-alkoxybuta-1,3-diene as concentrated residue obtained according to Reference Example 1 was added dropwise to the solution, and stirred at a temperature of 27 to 30° C.

The reaction took 31 hours until the end point thereof was confirmed in HPLC analysis with L-Column-ODS, and the optical purity based on CHIRALPAK AD was 7.2% ee.

Comparative Example 2

Experiment in which Lithium Chloride was Added and N,N,N',N'-tetramethylethylenediamine was not Added Under nitrogen atmosphere, 1.0 g (3.15 mol) of (E)-3-[2-cyclopropyl-4-(4-fluorophenyl)-quinolin-3-yl]-prop-2-en-1-al was dissolved in 12 mL of tetrahydrofuran. To the solution, 42.57 mg (0.0945 mmol) of optically active binaphthol-titanium complex powder prepared by reacting (S)-(−)-1,1'-bi-2-naphthol with titanium tetraisopropoxide in dichloromethane and then evaporating the solvent was added at first, and then 40.2 mg (0.945 mmol) of lithium chloride was added, and 1.73 g (6.3 mmol) of 1,3-bis(trimethylsilyloxy)-1-alkoxybuta-1,3-diene as concentrated residue obtained according to Reference Example 1 was added dropwise to the solution, and stirred at a temperature of 27 to 30° C.

The reaction took 70 hours until the end point thereof was confirmed In HPLC analysis with L-Column-ODS, and the optical purity based on CHIRALPAK AD was 92.7% ee or more.

Comparative Example 3

Experiment in which N,N,N',N'-tetramethylethylenediamine was Added and Lithium Chloride was not Added Under nitrogen atmosphere, 1.0 g (3.15 mol) of (E)-3-[2-cyclopropyl-4-(4-fluorophenyl)-quinolin-3-yl]-prop-2-en-1-al was dissolved in 12 mL of tetrahydrofuran. To the solution, 42.57 mg (0.0945 mmol) of optically active binaphthol-titanium complex powder prepared by reacting (S)-(−)-1,1'-bi-2-napthol with titanium tetraisopropoxide in dichloromethane and then evaporating the solvent was added at first, and then 292.92 mg (2.52 mmol) of N,N,N',N'-tetramethylethylenediamine were added, and 1.73 g (6.3 mmol) of 1,3-bis(trimethylsilyloxy)-1-alkoxybuta-1,3-diene as concentrated residue obtained according to Reference Example 1 was added dropwise to the solution, and stirred at a temperature of 27 to 30° C.

The end point of the reaction could not be confirmed by 94 hours after the reaction was started in HPLC analysis with L-Column-ODS, and the optical purity based on CHIRALPK AD was 94.3% ee or more.

INDUSTRIAL APPLICABILITY

According to the present invention, optically active (E)-7-[2-cyclopropyl-4-(4-fluorophenyl) quinolin-3-yl]-5-hydroxy-3-oxohept-6-enoic acid esters which have high optical purity of 99% ee or more can be obtained in a high yield of 90% or more, and therefore can be sufficiently used as an intermediate for synthesizing (3R, 6S, 6E)-7-[2-cyclopropyl-4-(4-fluorophenyl)quinolin-3-yl]-3,5-dihydroxyhept-6-enoic acid salt useful for prevention and treatment of hyperlipidemia, arteriosclerosis or the like. Consequently, the optically active (E)-7-[2-cyclopropyl-4-(4-fluorophenyl) quinolin-3-yl]-5-hydroxy-3-oxohept-6-enoic acid esters obtained according to the present invention are industrially useful.

The invention claimed is:

1. A process for producing an optically active (E)-7-[2-cyclopropyl-4-(4-fluorophenyl) quinolin-3-yl]-5-hydroxy-3-oxohept-6-enoic acid ester of formula (III)

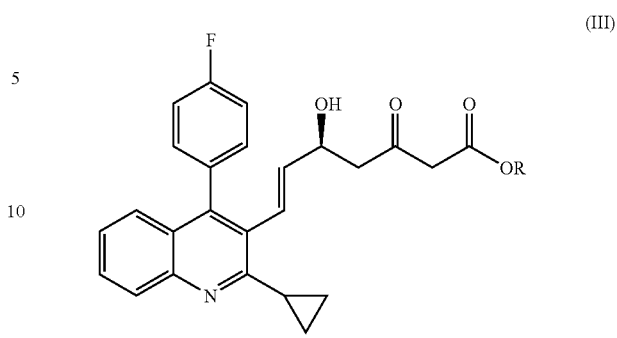

wherein R is an alkyl having 1 to 4 carbon atoms, which comprises reacting 1,3-bis(trimethylsilyloxy)-1-alkoxybuta-1,3-diene of formula (I)

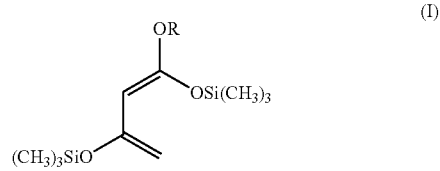

wherein R is as defined above, with (E)-3-[2-cyclopropyl-4-(4-fluorophenyl)-quinolin-3-yl]-prop-2-en-1-al of formula (II)

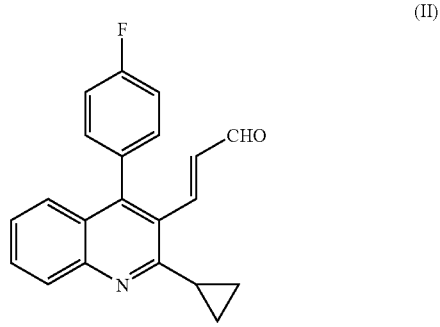

in the presence of an optically active binaphthol-titanium complex prepared by reacting 1,1'-bi-2-naphthol with titanium tetraisopropoxide, a metal salt and an amine, and then subjecting the resulting reaction product to desilylation.

2. A process according to claim 1, wherein the metal salt is lithium chloride, lithium bromide, lithium acetate, lithium hydroxide, lithium borate, lithium phosphate, sodium chloride, potassium chloride, magnesium chloride, aluminum chloride or copper chloride.

3. A process according to claim 1, wherein the amine is N,N,N',N'-tetramethylethylenediamine, diisopropylethylamine, pyridine, 4-dimethylaminopyridine, triethylamine or morpholine.

4. A process according to claim 1, wherein the metal salt is lithium chloride and the amine is N,N,N',N'-tetramethylethylenediamine.

* * * * *